US00PP13960P29

(12) United States Plant Patent
Olsthoorn

(10) Patent No.: US PP13,960 P2
(45) Date of Patent: Jul. 8, 2003

(54) SPATHIPHYLLUM PLANT NAMED 'SWEET BENITO'

(75) Inventor: Petrus C. M. Olsthoorn, Monster (NL)

(73) Assignee: Pothos Plant B.V., Honselersdijk (NL)

( * ) Notice: Subject to any disclaimer, the term of this patent is extended or adjusted under 35 U.S.C. 154(b) by 0 days.

(21) Appl. No.: 10/076,387

(22) Filed: Feb. 19, 2002

(51) Int. Cl.[7] ..... A01H 5/00

(52) U.S. Cl. ..... Plt./364

(58) Field of Search ..... Plt./364

(56) References Cited

PUBLICATIONS

UPOV–ROM GTITM Computer Database 2002/03, GTI Jouve Retrieval Software, Citation for Spathiphyllum 'Sweet Benito'.*

* cited by examiner

*Primary Examiner*—Bruce R. Campell
*Assistant Examiner*—June Hwu
(74) *Attorney, Agent, or Firm*—Foley & Lardner

(57) ABSTRACT

A new and distinct Spathiphyllum plant named 'Sweet Benito' characterized by having early shoot production, dark and glossy leaves, long-lasting inflorescence color and duration, high inflorescence production, compact plant size, and good light sensitivity/resistance of leaves.

2 Drawing Sheets

Latin name of the genus and species of the plant claimed: Spathiphyllum hybrid.

Variety denomination: 'Sweet Benito'.

BACKGROUND OF THE INVENTION

The present invention relates to a new and distinct cultivar of Spathiphyllum plant, hereinafter referred to by the cultivar name 'Sweet Benito'.

The new cultivar originated from a cross made in a controlled breeding program in Monster, The Netherlands. The female parent is '94225-1' (unpatented). The male parent is '93165-16' (unpatented). 'Sweet Benito' was discovered and selected by the inventor, Petrus C. M. Olsthoorn, as a flowering plant within the progeny of the stated cross in a controlled environment in Monster, The Netherlands.

Asexual reproduction of the new cultivar was first performed by tissue culture in week 16 of 1997 in Honselersdijk, the Netherlands and has demonstrated that the combination of characteristics as herein disclosed for the new cultivar are firmly fixed and retained through successive generations of asexual reproduction and reproduces true-to-type.

BRIEF DESCRIPTION OF THE INVENTION

The following traits have been repeatedly observed and are determined to be basic characteristics of 'Sweet Benito' which in combination distinguish this Spathiphyllum as a new and distinct cultivar:

1. Early shoot production;
2. Dark and glossy leaves;
3. Long-lasting inflorescence color and duration;
4. High inflorescence production;
5. Compact plant size; and
6. Good light sensitivity/resistance of leaves.

'Sweet Benito' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Honselersdijk, The Netherlands under conditions which closely approximate those generally used in commercial practice.

Of the many commercial cultivars known to the present inventor, the most similiar in comparison to 'Sweet Benito' is the cultivar 'Cupido' (unpatented). 'Sweet Benito' produces shoots early, within fifteen weeks after tissue culture the first one appears. 'Sweet Benito' has darker and glossier leaves than 'Cupido'. The white inflorescence color of 'Sweet Benito' lasts longer than the inflorescence color of 'Cupido'. The inflorescence of 'Sweet Benito' is a little smaller and rounder than that of 'Cupido'. 'Sweet Benito' produces 8–15 inflorescences (depending on pot size) whereas 'Cupido' produces between 8 and 10. 'Sweet Benito' produces up to 8 inflorescences at once whereas 'Cupido' produces only 2 to 3 inflorescences at once. Plant height of 'Sweet Benito' is approximately 60 percent that of 'Cupido's'. The leaves of 'Sweet Benito' are narrower than the leaves of 'Cupido'. The main leaf vein of 'Sweet Benito' is lighter in color than the leaves themselves whereas the main leaf vein color of 'Cupido' is the same color as the leaves. 'Cupido' is more sensitive to light than 'Sweet Benito' causing the color of the leaves of 'Cupido' to lighten faster. Finally, in order to get the shoots of a Spathiphyllum to flower, gibberellic acid is added. 'Cupido' needs more than twice the concentration of this hormone than 'Sweet Benito' to get the same result.

BRIEF DESCRIPTION OF THE DRAWINGS

The accompanying photographic illustrations show a 23-week old plant of 'Sweet Benito'.

The first drawing shows a 'Sweet Benito' plant on the left and a close up of its inflorescence on the right.

The second drawing shows a 'Sweet Benito' plant on the left with a 'Cupido' plant on the right.

DETAILED BOTANICAL DESCRIPTION

The following observations, measurements and values describe the new cultivar at 23 weeks as grown in Honselersdijk, The Netherlands under conditions which closely approximate those generally used in commercial practice. Grown in standard glasshouses in well-drained cocos, pH values in cocos/peat soil (50/50) is 6.0–6.2 and 5.8–6.0 in potting soil. Base fertilizing (PG-mix) is 0.75 kgs in cocos/peat soil as well as in potting soil. This species needs careful fertilizer treatment; a mix of calcium nitrate, iron chelate (EDDHA and DTPA), magnesium sulphate, mono potassium phospate, potassium nitrate, borax, manganese, molybdenum and copper sulphate. Ideal growing conditions under which this plant is grown is 21–23 degrees Celsius during the day and 20 degrees Celsius at night. For flower initiation '54905' gets 40 ppm of gibberalic acid (depending on the pot size, plant development and age of plant). Color references are made to The Royal Horticultural Society Colour Chart (R.H.S.), except where general colors of ordinary significance are used. Color values were taken under daylight conditions at approximately 3 p.m. in Boskoop, The Netherlands.

Origin: Honselersdijk, The Netherlands, November 2001.

Parentage:

*Male parent.*—'942251'.

*Female parent.*—'93165-16'.

Classification:

*Botanical.*—Spathiphyllum.

*Commercial.*—Spathiphyllum cv. Sweet Benito.

Propagation: By tissue culture.

Plant:

*Appearance.*—Broad and upright with leaf petioles growing directly from base.

*Height.*—Average 35 cm (excluding flowers).

*Width.*—Average 55 cm.

*Growth habit.*—Moderately vigorous.

*Time of flowering.*—18–19 weeks after potting of a 20 cm cutting.

*Winter hardiness.*—USDA Zone 10.

*Stems.*—Leaves grow directly from base, so no stems are visible.

*Roots.*—Time to initiate roots: 1–2 weeks under 21–23 degrees Celsius (day) and 20 degrees Celsius at night. Time to develop roots: 3–4 weeks under 21–23 degrees Celsius (day) and 20 degrees Celsius at night. Rooting habit: Freely branching.

Foliage:

*Shape.*—Narrow elliptic to lanceolate.

*Apex.*—Narrow acute to slightly apiculate.

*Base.*—Attenuate.

*Texture.*—Smooth, glossy, somewhat leathery.

*Leaf color.*—Upper surface: Green to yellow-green, darker than but closest to RHS 139A to RHS 147A. Lower surface: Green to yellow-green, between RHS 137B and 146A.

*Midrib color.*—Upper Surface: Green RHS 143A to RHS 143B. Lower Surface: Yellow-green RHS 144B.

*Size of leaf.*—Width: Average 8 cm. Length: Average 28 cm. Petiole: Average length 18 cm, average diameter 3 mm, rounded, green in color RHS 141A to RHS 143A.

*Petiole sheath.*—Average 14 cm long and 7 mm wide (measured at halfway point).

*Geniculum.*—Average length 2.7 cm, average width 4 mm, green in color RHS 143A to RHS 143B.

*Veins.*—Average 10 pairs of furrowed secondary veins, upper side color green to yellow-green, closest to but darker than RHS 139A to RHS 147A, under side color green RHS 143B.

Inflorescence description:

*Immature.*—Peduncle: Average length 41 cm, average diameter 4 mm, rounded, green in color RHS 143A to RHS 143B. Spathe: Average length 13 cm, average width 5.5 cm, cupped, average depth 1.5 cm.

*Mature.*—Spathe: Size: Average length 15 cm, average width 6 cm, cupped, average depth 1.7 cm. Color: Unopened Bud: White, closest to RHS155A. Fully Open: Front Surface and Midrib: White, closest to RHS 155A. Back Surface: White, closest to RHS 155A, midrib green at base RHS 142A. Apex: Apiculate, only the tip is green RHS 143A. Faded: Front Surface: Yellow-green, paler than but closest to RHS 145D, turning brown RHS 199A with age. Back Surface: Yellow-green, RHS 145D, turning brown RHS 199A to RHS 199B. Apex: Green, RHS 143A.

*Arrangement.*—Solitary.

*Shape.*—Broad lanceolate, base decurrent.

*Margins.*—Entire.

*Fragrance.*—Sweet.

*Lastingness of the individual inflorescence.*—On average over two weeks.

Reproductive organs:

*Spadix.*—Size: Average length 3.5 cm, average width 1.4 cm. Quantity: Average 60 individual flowers per spadix. Color: Greyed-yellow, RHS 160D. Stamens: 6, pressed against styles. Pistil: Each individual flower has one pistil with a tri-parted stigma; the pistil has an average length of 2 mm and is greyed-yellow in color, RHS 160D.

*Pollen.*—Yellow-white RHS 158A.

Seed production: No observations to date.

Fruit production: No observations to date.

Disease resistance/susceptibility: No observations to date.

I claim:

1. A new and distinct Spathiphyllum plant named 'Sweet Benito', substantially as illustrated and described herein.

* * * * *

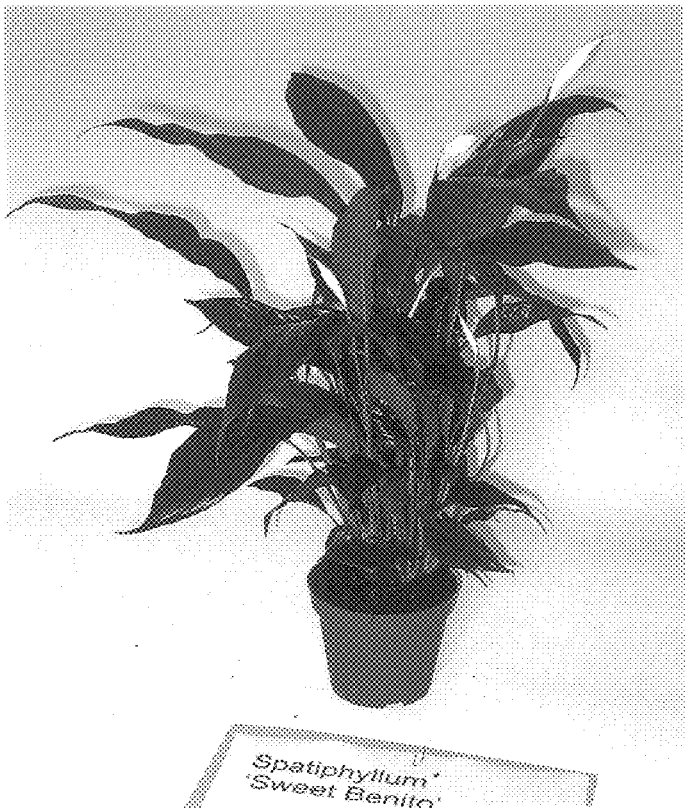
Spatiphyllum'
'Sweet Benito'
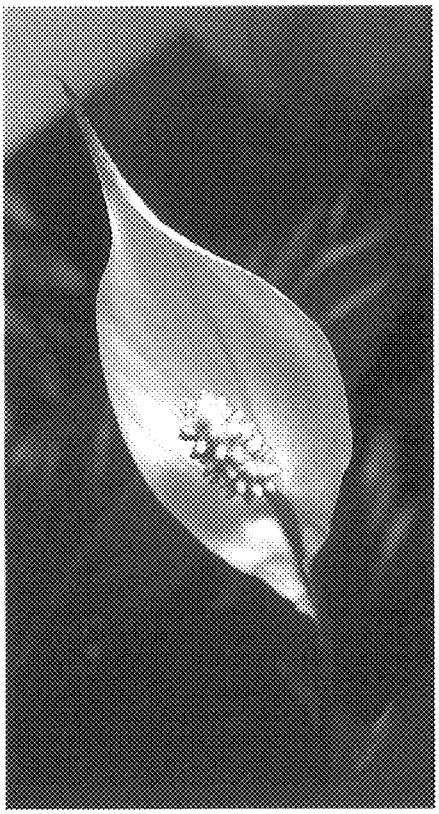

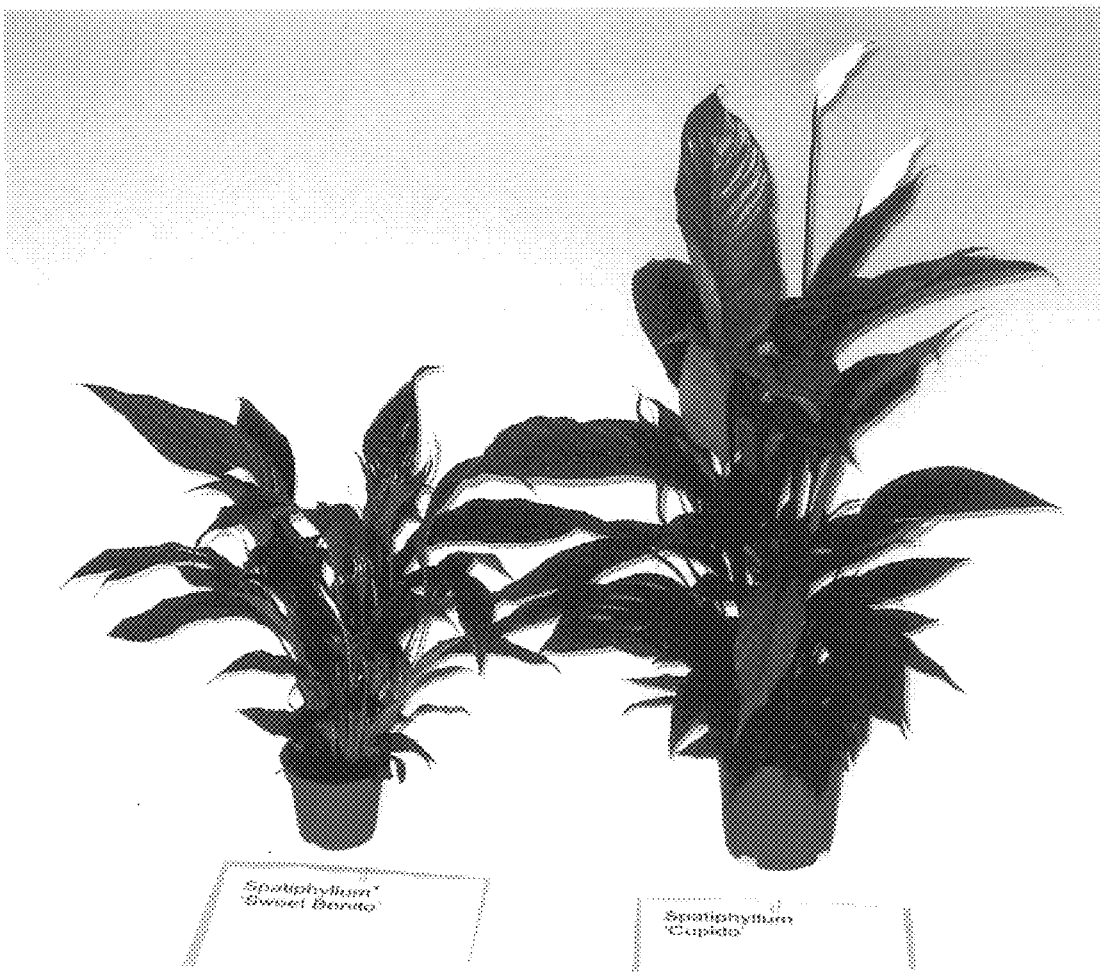
Spathiphyllum
'Sweet Benito'
Spathiphyllum
'Capido'